(12) United States Patent
Hunter et al.

(10) Patent No.: US 10,499,882 B2
(45) Date of Patent: Dec. 10, 2019

(54) METHODS AND SYSTEMS FOR ULTRASOUND IMAGING

(71) Applicant: yoR Labs, Inc., Portland, OR (US)

(72) Inventors: Valerie Hunter, Portland, OR (US); Clark Brooks, Hillsboro, OR (US); Anshumali Roy, Portland, OR (US)

(73) Assignee: yoR Labs, Inc., Portland, OR (US)

( * ) Notice: Subject to any disclaimer, the term of this patent is extended or adjusted under 35 U.S.C. 154(b) by 789 days.

(21) Appl. No.: 15/200,609

(22) Filed: Jul. 1, 2016

(65) Prior Publication Data

US 2018/0000453 A1    Jan. 4, 2018

(51) Int. Cl.
*A61B 8/00* (2006.01)
*A61B 8/08* (2006.01)

(52) U.S. Cl.
CPC .............. *A61B 8/468* (2013.01); *A61B 8/085* (2013.01); *A61B 8/0825* (2013.01); *A61B 8/463* (2013.01); *A61B 8/469* (2013.01); *A61B 8/5207* (2013.01); *A61B 8/565* (2013.01)

(58) Field of Classification Search
IPC ....................................................... A61B 8/00
See application file for complete search history.

(56) References Cited

U.S. PATENT DOCUMENTS

| | | | |
|---|---|---|---|
| 6,063,030 | A | 5/2000 | Vara |
| 12,097,626 | | 12/2008 | Jago |
| 8,517,946 | B2 | 8/2013 | Kim |
| 9,132,913 | B1 | 9/2015 | Shapiro |
| 9,323,445 | B2 | 4/2016 | Kritt |
| 9,342,156 | B2 | 5/2016 | Huh |
| 2007/0259158 | A1 | 11/2007 | Friedman |
| 2011/0208052 | A1 | 8/2011 | Entrekin |
| 2013/0227052 | A1* | 8/2013 | Wenzel ............... H04L 67/1097 709/213 |
| 2013/0253317 | A1 | 9/2013 | Gauthier |
| 2014/0035916 | A1* | 2/2014 | Murphy .................. G06T 15/08 345/427 |
| 2014/0164965 | A1 | 6/2014 | Lee |
| 2017/0090571 | A1* | 3/2017 | Bjaerum ................. G06F 3/016 |

* cited by examiner

*Primary Examiner* — Pierre E Elisca

(74) *Attorney, Agent, or Firm* — Knobbe, Martens, Olson & Bear, LLP

(57) ABSTRACT

Described herein is a method and system for capturing, labeling, measuring and/or comparing images from current and/or previous ultrasound studies using a touch-screen user interface and a display where actions on the touch-screen input data on a captured ultrasound image on the display. Labels and measurements input on the touch-screen user interface are placed in the appropriate location on the captured ultrasound image and on an anatomically matching graphical representation on the touch-screen user interface either or both of which may be used to generate documentation and reports of an ultrasound study.

21 Claims, 12 Drawing Sheets

METHODS AND SYSTEMS FOR ULTRASOUND IMAGING

BACKGROUND

Ultrasound imaging is used in the diagnosis, screening, and treatment of a variety of diseases and conditions. An ultrasound image is created by transmitting sound waves into the body and then interpreting the intensity of the reflected echoes. The echoes are commonly used to produce two dimensional, three-dimensional, and color flow images of internal anatomical features of patients.

Current ultrasound systems often require an operator to hold an ultrasound probe in one hand while entering information onto a control panel with the other, frequently non-dominant, hand. As the number of functions performed by ultrasound systems increases, the size and complexity of the user interface, i.e. the control panel also increases. This complexity makes it inefficient and time consuming to acquire and optimize images and enter the data for each captured image.

Every image requires at least two labels which are typically typed by the sonographer with his or her left hand. Additionally, there are a variety of measurements which the sonographer obtains by manually placing electronic calipers on the image. The process of optimizing the image, labeling, and measuring is cumbersome, time consuming and prone to errors. There is therefore a need for an ultrasound system that provides the operator with a more streamlined method and interface for optimizing the image, labeling, and making measurements in ultrasound images.

BRIEF SUMMARY

Provided herein is a system and method for annotating an ultrasound image frame in an active ultrasound scan. The system comprises a first display device and a control device with a touch screen user interface. In some embodiments, the system may further comprise ancillary devices such as, but not limited to, a keyboard, mouse, track ball and the like. In some embodiments, the ultrasound image on the first display device may be optimized using optimization controls on the user interface including, but not limited to, focal zone, time gain compensation, dynamic range, frame rate, Doppler gain, and field width. The control device displays a proportional graphical representation of the anatomical feature being scanned. By interacting with the graphical representation of the anatomical feature, labels and other information may be placed on an ultrasound image in the active ultrasound scan on the first display device. Interactions with the graphical representation of the anatomical feature comprise a touch gesture on the user interface with a stored image manipulation function such that each type of touch gesture is correlated to a different image manipulation function and applies the image manipulation function to the ultrasound image and/or the graphical representation of the anatomical feature being scanned. Such information may include, but is not limited to, the presence of a lesion, the size of the lesion, the location of a lesion, type of lesion, distance from anatomical landmarks, transducer direction and the like. The label applied to the ultrasound image may be entered using a gesture, chosen from a word bank, chosen from a set of structure labels, or entered manually through the use of a touch screen or ancillary keyboard. In some embodiments, subsequent touch gestures on the user interface modify the label of the lesion on the displayed active ultrasound image.

In addition to an active ultrasound scan, manipulable thumbnails of images from prior generated scans from one or more prior studies and images from the current scans of the anatomical feature under examination may be displayed on the first display device. Such images may be manipulated by actions on the user interface and/or through interaction with an ancillary device.

In some embodiments, the active ultrasound image may be reproduced on a touchpad surface on the user interface. By interacting with the touchpad surface, the relative depth of the lesion in the anatomical feature being scanned may be captured.

The information placed on the active ultrasound image and/or the graphical representation of the anatomical feature being scanned may be captured in a worksheet. Such a worksheet may be used to provide a reference for the individual reviewing the ultrasound or may be produced as a final report ready for signature by the individual reviewing the ultrasound.

In some embodiments, a computer operated method of running a visualization application on the computer to compare prior generated images of an anatomical feature during an active scan may include displaying patient information on a first device that has been inputted through a user interface, receiving an input of the anatomical feature, retrieving a series of prior generated ultrasound images of the anatomical feature, determining the ultrasound images matching the labels from the prior generated worksheet from the series of prior generated ultrasound images of the anatomical feature, displaying a graphical representation of the anatomical feature on the user interface, populating the graphical representation of the anatomical feature with labels from a prior generated worksheet, marking a lesion matching the labels from the prior generated worksheet on the active scan, and/or comparing changes in the anatomical feature. In some embodiments, the imported labels on the graphical representation are modified to indicate the current labels on the active scan. The changes include, but are not limited to, additional lesions, change in size, and change in composition of prior lesions.

An ultrasound system may include an ultrasound probe, a first processor configured to form an ultrasound image from the ultrasound data, a first display screen divided into a group of sectors, each sector displaying different information, a touch-screen user interface, and/or a second processor that receives input from the touch-screen user interface. The ultrasound probe may include a transducer configured to transmit an ultrasound signal to a target object, receive an ultrasound echo signal reflected from the target object, and form ultrasound data corresponding to the target object.

In some embodiments, in response to receiving input from the touch-screen user interface, the second processor sends a signal to a labeling module to input labels and measurements of the target object on an image on the first display screen and a graphical representation of the anatomical feature on a user interface.

Information in the sectors of the first display screen may include, but are not limited to, the information is an active scan, captured images from the active scan, and images from previous scans of a same anatomical feature of a same individual.

The touch-screen user interface may include a graphical representation of an anatomical feature, a track pad, a keyboard, a word bank, a structured label bank, image optimization controls, and a series of drop-down menus with additional control options. In some embodiments, the touch-screen user interface may further include a measuring apparatus that calculates a distance between two fingers placed on the measuring apparatus and places a measurement for an anatomical feature on a label on the ultrasound image. In some embodiments, the labels applied to the active ultrasound image may appear at a comparable location on the graphical representation of the anatomical feature.

To the accomplishment of the foregoing and related ends, certain illustrative aspects of the system are described herein in connection with the following description and the attached drawings. The features, functions and advantages that have been discussed can be achieved independently in various embodiments of the present disclosure or may be combined in yet other embodiments, further details of which can be seen with reference to the following description and drawings. This summary is provided to introduce a selection of concepts in a simplified form that are elaborated upon in the Detailed Description. This summary is not intended to identify key features or essential features of any subject matter described herein.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
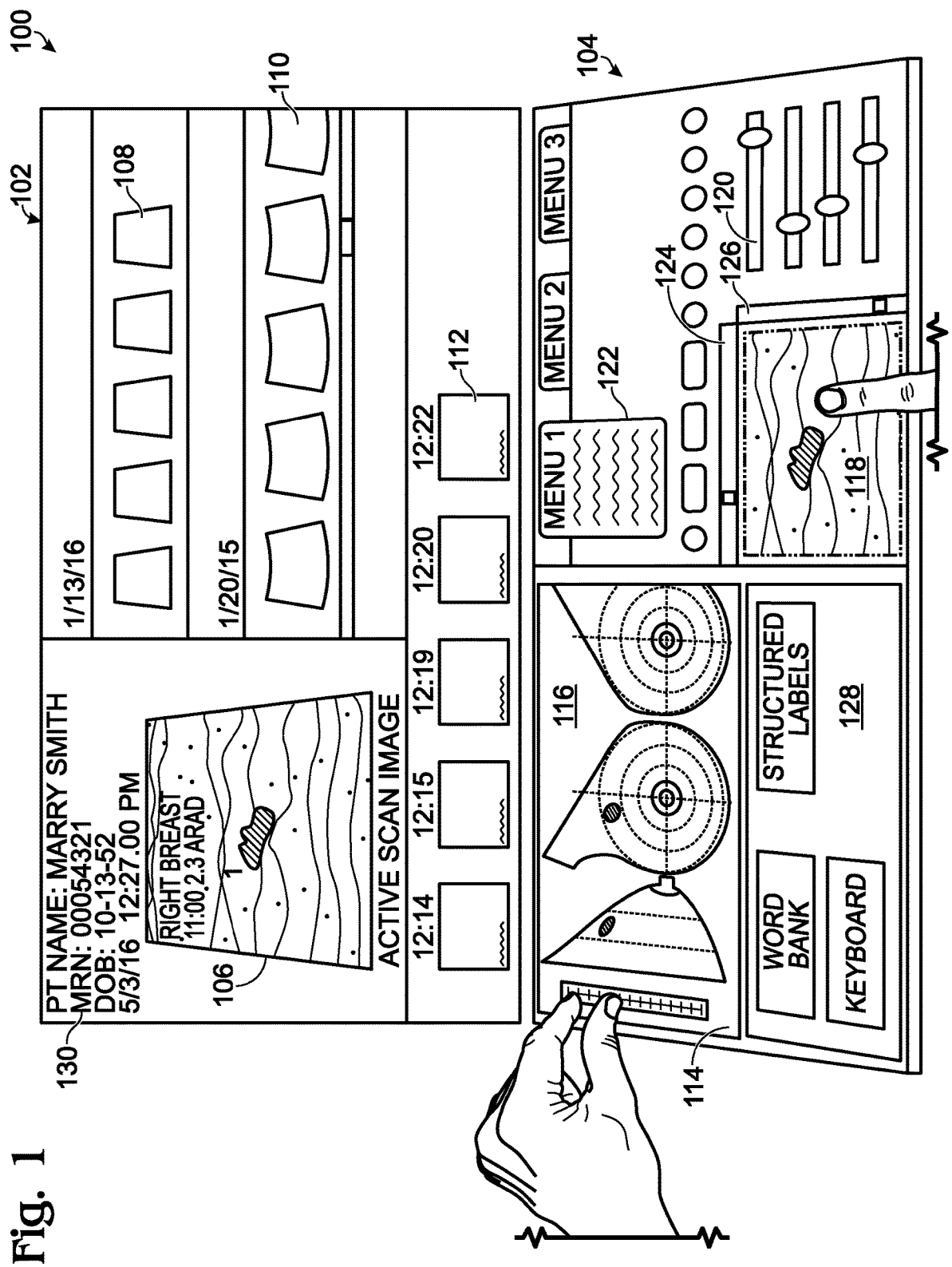
FIG. 1 illustrates an embodiment of information that may be displayed on a display and user interface.

"Database" in this context refers to an organized collection of data (states of matter representing values, symbols, or control signals to device logic), structured typically into tables that comprise 'rows' and 'columns.'

"Final Report" in this context refers to the final product of an ultrasound scan including written documentation of the imaging findings and an impression or diagnosis based on those findings.

"Graphical representation" in this context refers to a stylized drawing of the body part being scanned.

"Module" in this context refers to logic having boundaries defined by function or subroutine calls, branch points, application program interfaces, or other technologies that provide for the partitioning or modularization of particular processing or control functions. Modules are typically combined via their interfaces with other modules to carry out a machine process.

"Reader" in this context refers to the person interpreting the ultrasound scan.

"Scan plane" in this context refers to the orientation of the ultrasound probe relative to the part being scanned.

"Structured labels" in this context refers to a list of labels used for a specific exam type in which the labels are automatically presented in a set order.

"Touch screen" in this context refers to a capacitive or resistive display which responds to direct touch manipulation, either by finger (simple or multi-touch), stylus, or both. The user can use the touchscreen to react to what is displayed and to control how it is displayed. The touchscreen enables the user to interact directly with information displayed rather than using a mouse, touchpad, or other intermediate device (with the exception of a stylus).

"Ultrasound study" in this context refers to a diagnostic procedure performed by a sonographer that uses two-dimensional images produced by inaudible sound waves to evaluate an anatomical feature.

"User" in this context refers to the person actually performing the ultrasound scan.

"Word bank" in this context refers to a list of context-specific labels which are commonly used for a specific scan type or body part.

"Worksheet" in this context refers to a generated document comprising patient information, scan information, and images and written findings from the ultrasound.

DESCRIPTION

Described herein is an ultrasound imaging system and means for recording, comparing, labeling, reporting and/or documenting information received from an ultrasound probe. Further provided is a system including an ultrasound probe comprising a transducer configured to transmit an ultrasound signal to a target object, receive an ultrasound echo signal reflected from the target object, and form ultrasound data corresponding to the target object. The system includes a first processor configured to form an ultrasound image from the ultrasound data; a first display screen; a user interface including a touch-screen and a second processor that receives input from the user interface. A plurality of activation areas on the user interface allow for interaction with one or more ultrasound images and diagrams on the first display screen and the user interface. In some embodiments, the first and second processor may be a single processor. A labeling module may be activated by the user interface to add the appropriate labels to the active ultrasound image and to a graphical representation of the target object. A computer visualization application operated via the user interface allows for the manipulation and comparison of data on both the first display and the user interface.

The first display screen may be any type of screen device including a tablet, touchscreen, flat screen, LED screen, electroluminescent display, organic LED, LCD, virtual display and the like. The first display may present information in a variety of ways. In some embodiments, the first display screen is divided into a plurality of sectors in any order each of which may contain one or more of: the patient information, the active ultrasound image being currently acquired from a machine transformation of an ultrasound reading in process (active scan), thumbnails of prior studies including studies performed on machines other than ultrasound machines, and thumbnails of recorded images from the current exam. In some embodiments, the thumbnails may be presented in chronological order. In other embodiments, the thumbnails may be presented in an order chosen by the user. Each thumbnail image may be expanded, moved, or removed as desired using gestures on the user interface. In some embodiments, the thumbnails may be stacked one on top of each other with the most recent scan on top. In other embodiments, thumbnails may be presented in discrete rows. Thumbnails may be labeled with the date and time of the scan as well as any other relevant label or descriptive information including, but not limited to, patient information, scan location, scan date, scan plane, anatomical subject of the scan, presence or absence of lesions, purpose of the scan, measurements of lesions, number of lesions and the like.

The content of the first display is controlled by a user interface such as a touch-screen user interface that allows the user to manipulate the images on the first display. Touch-screen based computers comprise computer assemblies combining an internal computer processor and touch sensitive digital display screen. They commonly also have access to cloud based storage and computing support and wireless connectivity and may include voice recognition. The digital display and the computer's ability to monitor the positions and motions of finger touches on the touch-screen are coordinated such that finger contact locations can be correlated by the computer with the information displayed at those locations. A variety of gestures may be used to interact with the user interface, including, but not limited to, touching, swiping, double tap, multiple finger taps, pinch, multitouch, radio buttons and the like. A processor is coupled to the touch-screen for detecting a touch by the user on the touch-screen that identifies a selected activation area. The processor then performs the device function associated with the stored image manipulation function thereby activating the selected activation area. In some embodiments, the user may interact with the user interface through voice recognition, a stylus, keyboard, mouse, virtual reality headset, hand gestures in the air, any other way generally used to interact with a user interface, or a combination thereof. In some embodiments, controls on the ultrasound probe may be used to input information onto either or both the user interface and the display screen.

The touch-screen user interface as described herein is divided into a plurality of control sectors including, but not limited to, a proportionate graphical representation of the anatomical part being scanned, a scale or other measuring apparatus, a track pad, a series of one or more virtual controls such as buttons or radio buttons, word bank, structured label bank, tabbed drop down menus, virtual keyboard, active ultrasound image, virtual trackpad, virtual depth and focus sliders, virtual cine slider, and virtual time gain compensation sliders. In some embodiments, the number and arrangement of control sectors may be altered to suit the needs of the user. For example, during a scan, it may be desirable to have an extended display of one or more of the control sectors. In some embodiments, there may be one control sector. In other embodiments, there may be 2, 3, 4, 5, 6, 7, 8, 9, 10, 11, 12 or more control sectors. Activation of each sector on the user interface performs a function on the user interface and manipulates information on the first display screen and/or the user interface. In some embodiments, information may be entered by using a physical keyboard.

Patient information is input through the touch-screen. In some embodiments, patient information may be part of a database that is part of the ultrasound imaging system. In other embodiments, patient information and prior scans are retrievable from a network based database. For example, in a hospital, there is a typically a network-attached server that stores patient information, images and image acquisition settings such that they can be accessed from imaging devices in different locations. Once patient information is inputted through the touch-screen display and the scan type is indicated, the visualization application on the touch-screen populates the touch-screen with a graphical representation of the location of the anatomical scan, and populates one or more of the word bank, structured label bank, and drop down menus with context-specific labels pertinent to the anatomical location. If prior scans have been performed, the display presents a list of prior scans that may be selected for comparison to images from the active scan. In some embodiments, the system may tag suggested comparison scans which can be accepted or rejected by the user.

Useful ultrasound images require at least two labels: the anatomical region being imaged and the scan plane or transducer orientation. Additional information that may be included with an image includes, but is not limited to, measurements of an anatomical feature of interest including the longest horizontal diameter, the anteroposterior diameter, and the orthogonal horizontal; the location of the anatomical feature of interest in reference to anatomical landmarks (such as the chest wall); the type of lesion or anatomical feature of interest; the orientation of the lesion of interest; the location and depth of the lesion of interest and the like.

An anatomical feature of interest may include in its label whether it is transverse (TR) or longitudinal (LG) indicating the direction of the scan; whether the lesion is a cyst, mass, duct or blood vessel; whether it is located anterior to or posterior to an anatomical landmark; its size and the like. For example, in a breast ultrasound, an anatomical feature of interest may include in its label whether it is the right or left breast, the clock face location in the breast, whether the scan plane is radial (RAD), anti-radial (AR-ARAD), transverse (TR), longitudinal (LG), and/or descriptive labels such as whether the lesion is a cyst, mass, duct or blood vessel, whether it is located anterior to or posterior to an anatomical landmark such as the nipple or chest wall, the measurements and number of lesions, and the like.

In some embodiments, structured labels, a word bank, or keyboard for manual entry of a label may be used to add information to labels or to modify existing information on a label regarding the active scan. In some embodiments, labels for all body parts are listed. In some embodiments, where there are a finite number of anticipated or commonly used labels for a specific anatomical feature, the labels may be listed in a word bank. For example a word bank for a breast study may include, but is not limited to, RAD, ARAD, SAG, TRAN, Axilla, Axillary tail, Subareolar, Inframammary fold, Anterior Axillary line, Middle Axillary line, Posterior Axillary line, Palp, Palp area, Tract, Calcifications, Heel rock, Toe rock, Skin fascia, Chest wall, Lateral to, Medial to, Cyst, Foam cyst, FA, Mass, Halo, Typical, swirling echoes, and vessel. A word bank for a thyroid study may include, but is not limited to, Right, Left, SAG, TR, Isthmus, upper pole, mid gland, lower pole, Esophagus, Cyst, Cystic changes, Microcalcifications, Thyroid bed, and Lower pole obscured by clavicle. A word bank for a cervical node study may include, but is not limited to, Cyst, Cystic changes, Calcification, Microcalcifications, Hilar flow, Cortical flow, and Thyroid bed.

Structured labels may be used where a scan generally proceeds in a standard order and typical images are acquired. Standardized labels may appear in order and the user merely accepts the labels. Common scan types for structured labeling would include, but are not limited to, obstetrics, abdomen, carotid, lower extremity venous among others. The order and the labels in the structured label list may be fixed or customizable. In some embodiments, structured labels for an obstetric scan for maternal and fetal anatomy may be customized to be presented in the order the sonographer usually scans: for example, cervix, placenta trans, placenta long, ventricles, CSP, CM, orbits, face, N/L and profile, among others. For a thyroid study, the structured labels presented may include, but are not limited to, Right, RUP TR, R mid TR, RLP TR, R SAG lat, R SAG ML, R SAG med, R Level IV LN, Isthmus TR, Isthmus SAG, Left, LUP TR, L mid TR, LLP TR, L SAG med, L SAG ML, L SAG lat, and L Level IV LN. The structured labels for a cervical node study may include, but are not limited to, Right Neck with sub labels including Level I, TR; Level I, LG; Level IIA, TR; Level IIA, LG; Level IIB, TR; Level IIB, LG; Level III, TR; Level III, LG; Level IV, TR; Level IV, LG; Level V, TR; Level V, LG; Level VA, TR; Level VA, LG; Level VI TR; Level VI, LG; Thyroid bed, TR; and Thyroid bed, LG. The Left Neck may appear with sub labels including, but not limited to, Level I, TR; Level I, LG; Level IIA, TR; Level IIA, LG; Level IIB, TR; Level IIB, LG; Level III, TR; Level III, LG; Level IV, TR; Level IV, LG; Level V, TR; Level V, LG; Level VA, TR; Level VA, LG; Level VI TR; Level VI, LG; Thyroid bed, TR; and Thyroid bed, LG. Labels may also include numbers indicating the presence of a plurality of lesions and providing reference tags for follow up studies of each lesion. In some embodiments, each lesion may be numbered automatically.

Identification labeling of the scan image on the display may occur by interacting in one or more ways with the touch-screen user interface. For example, in some embodiments, placement of the identification labels may occur by tapping on the graphical representation on the user interface. When a location is tapped, a marker may appear on the graphical representation showing the location of the tap on the drawing and a location label corresponding to the marker may appear on the displayed active ultrasound image. The position of a label on the graphical representation may be re-positioned by selecting and dragging it. A directional swipe on the graphical representation may provide the scan plane label for the active image on the first display. If multiple lesions are being documented, the tap on the graphical representation may add a lesion number to the label on the active scan. In some embodiments, the same labels may appear on the graphical representation and the active scan when the graphical representation is manipulated. In other embodiments, different labels may appear on the graphical representation and the active scan. In further embodiments, some labels may appear on the graphical representation or the active scan, but not both. For example, transducer direction is necessary for the ultrasound image, but is less so for the graphical representation. In additional embodiments, a label placed on the active image may be copied on the matching location on the graphical representation. The annotated graphical representation may become part of a study and be used as a data summary and/or as part of a final report. In additional embodiments, indicating placement of a lesion on the graphical representation on the user interface will create a lesion number and will capture the measurements of the lesion. In some embodiments, the label may include one or more symbols indicating the type of lesion or anatomical part shown in the ultrasound. For example, there may be symbols for a mass, duct, vessel, cyst, malignancy, benign lesions, lymph nodes, and the like. Such symbols may be dragged, stretched, pinched, or otherwise manipulated to more closely resemble the placement, size and shape of the actual lesion.

In additional embodiments, smart comparisons of ultrasound images may be made. For example, a user may freeze a frame of the active scan and place identifying labels such as a location or body part on the image. A search is then initiated of each prior scan in the comparison display or database and prior images tagged with the same label or general location are collected. All prior images tagged with the same label or general location from prior scans may appear as chronologically ordered thumbnails. In another embodiment, pattern recognition may be used to locate or help locate relevant comparison images. For example, in the follow up for a cyst in the right ovary, once the scan in progress is tagged as "right ovary" all prior images of the right ovary may appear as thumbnails on the display. In another example, lesions may be compared, with a dialog box querying if the lesion is the same as the lesion in a comparison image or a new lesion. The lesion in the active scan may then be labeled as being the same or different as the lesion in the comparison image. In some embodiments, available prior images may include a standard set of "normal" images that may be used for training purposes, or to provide a standard reference for identifying abnormalities in a scan.

Many ultrasound scans require one or more measurements. In some embodiments, such measurements may be taken manually by measuring the distance on the patient with the left thumb and forefinger and tapping with the spaced thumb and forefinger in a two finger gesture on a measuring device such as a scale or ruler on the user interface. The user interface measures the distance tapped and adds the measurement to the current scan. Such measurements may be appropriately placed by dragging the measurement to the correct spot on a label or in a graphical representation. In other embodiments, a caliper may appear on the current scan and the caliper may be dragged or otherwise manipulated to the correct distance. In further embodiments, it may be desirable to take a plurality of measurements in various directions. Such a plurality of measurements may be labeled by number or other relevant information. In some embodiments, the creation of two or more measurements may be used to generate an ellipse between the calipers on the screen. The size and shape of the ellipse may be modified using finger motions such as pinch and spread on the user interfaces so that the ellipse surrounds the anatomical feature being measured as closely as possible. In a Doppler scan, calipers may measure properties related to Doppler velocities. In some embodiments, calipers placed on a Doppler waveform perform velocity calculations and waveform tracing. In additional embodiments, measurements on the active scan may be copied to the appropriate place on the graphical representation.

The data from an ultrasound is frequently preserved in a worksheet which generally contains the anatomical feature being scanned, patient identification, clinical indication, relevant clinical information, measurements, the graphical representation and any marks or labels on the graphical representation, and observations specific to the anatomical feature being scanned. Worksheets as described herein may additionally contain measurements from one or more prior scans increasing the ability to monitor the progression of a change in an anatomical feature. In some embodiments, the user may create a new blank worksheet based on the graphical representation or may import a worksheet from a prior scan. If it is a follow-up scan using an imported prior worksheet, the imported prior worksheet may be displayed on the user interface in lieu of a new blank graphical representation, along with prior labels, prior measurements and the dates of the scans. In some embodiments, prior data may be displayed in a different color or font than new information. In some embodiments, the user may then scan the anatomical feature, freeze an image and label the new images by tapping the appropriate location on the graphical representation and swiping the graphical representation to indicate transducer orientation. In other embodiments, the user may tap a target on the graphical representation and then scan to look for the lesion. The active image is then labeled using the information provided by the target location on the graphical representation. In some embodiments, when the active image is frozen, it then takes its label from the information provided from the prior scan by the target location on the graphical representation. These worksheets may be used to summarize data for a reader to use in compiling a report or may be signed as a final report.

As shown in FIG. 1, the ultrasound viewing system 100 has a display screen 102 and a user interface 104. Turning to the display screen 102, displayed in any order may be identifying information 130 including the time, date and patient information; active scan 106; thumbnails of images from current scan 112; thumbnails of relevant images from a first prior scan 108; and images from a second prior scan 110. Each scan section 108, 110 and 112 may be independently scrollable both sideways and up and down, allowing for viewing of more images than may fit in the space allotted on the display screen 102. Each image may additionally be enlargeable by manipulating a cursor on the display screen. In some embodiments a user may remove specific images from prior and/or the current scan from the display areas. The scrolling, enlargement or other manipulation of the images in the display may be performed in any way generally used. In some embodiments, the display may be a touch-screen. In other embodiments, the display screen 102 may be a traditional screen and the images may be controlled by another input device such as a mouse, trackball, and/or the user interface 104. While two rows of prior scans are shown in FIG. 1, any number of prior scans may be compared including 1, 2, 3, 4, 5, 6, 7, 8, 9, 10 or more prior scans. In some embodiments, prior scans organized by date may be available from drop down menus so that specific groups of scans may be chosen. In other embodiments, prior scans may be placed in successive rows as shown. In further embodiments, a plurality of prior groups of scans may be scrollable in the same or different rows.

When performing an ultrasound, an exam type may be selected, i.e. a particular location and/or body part. Once the exam type is selected, a list of dated prior studies for that patient may be shown from which the user can select the desired studies. The prior images from the selected studies may be displayed in any way that is useful. In some embodiments, the prior images may be stacked with the most recent first in the comparison frame on the display screen. In some embodiments, suggested comparison studies in a list may be highlighted. Prior studies may include prior ultrasound images as well as other imaging modalities such as mammograms, MRIs, CAT scans and the like.

The ultrasound viewing system 100 additionally includes a user interface 104. The user interface 104 is generally a touch-screen, but may be another type of display interface controlled by an ancillary device such as, but not limited to, a separate trackpad, mouse, trackball, stylus, keyboard, voice recognition, detection of motion in the air, or any other input modality. The user interface 104 allows the user to manipulate the images on the first display screen as well as perform other functions using control sectors.

As shown in FIG. 1, the user interface 104 includes an exemplary control sector of a graphical representation of the body part being examined 116. In this instance, the body part is the right breast. As shown in the active scan image in the display screen, there is a lesion present. By touching and swiping the graphical representation, the user may add a marker for the lesion and the lesion number to the graphical representation and may annotate the active ultrasound scan image 106 to include the lesion number, lesion location, and scan plane. The same labels as well as additional labels may be added to the graphical representation. The shape of the lesion on the graphical representation may be modified, if desired, to make it more closely resemble the actual lesion. In some embodiments, it may be possible to visually indicate the type of lesion including, but not limited to, a cyst, mast, duct, blood vessel and the like. In further embodiments, a directional swipe on the graphical representation will denote the transducer orientation, and the orientation is added to the lesion label on the ultrasound image. In additional embodiments, the system provides context-sensitive labels such as, but not limited to clock face location and general distance from the nipple on the breast graphical representation, cervical lymph node level on the neck graphical representation, location within the thyroid gland on the thyroid graphical representation, location in the carotid artery and the like. If there are multiple lesions, the labels will be numbered in addition to the other labeling information that is included. Label terms may automatically appear based on the type of exam and location of the lesion, may be selected from a word bank, may be selected from a structured labeling system or may be manually entered through the use of a keyboard. In some embodiments, it may be desirable to take multiple images of the same location using the same trajectory. It is therefore possible to preserve the labels from a prior captured image and replace the prior captured image with the next scanned image.

In one example, as shown in FIG. 1, the demographics of the patient are entered and the study type is selected using the user interface 104. Once "breast" is selected, a bilateral breast graphical representation appears on the user interface. The user taps the right breast on the graphical representation and the graphical representation changes to the right breast showing frontal and side views of the breast and labeling the graphical representation as "right breast." The right breast is scanned and shows a lesion in the right breast in the left upper outer quadrant in the active scan 106. The user taps at the location of the lesion on the graphical representation, producing a mark on the graphical representation indicating the site of the lesion and simultaneously a label on the active image indicating the location of the lesion. The user then swipes the graphical representation indicating transducer orientation. The transducer orientation label then appears on the ultrasound image but may or not may appear on the graphical representation. In some embodiments, the user may measure the physical distance of the lesion from the nipple and record the information using the exemplary control sector of a scale 114. The scale 114 allows the user to use their fingers to transfer a physical distance between the location of a lesion, as detected by ultrasound, and a physical landmark on the patient, in this case the nipple. The scale detects the finger positions and measures the distance between them, and then labels the ultrasound image with the measurement. In FIG. 1, active scan 106 would be labeled RT Breast, #1, 11:00, z.3, 3 cm FN, middle depth, ARAD, indicating that the image depicts the right breast, that it was the first lesion identified, it was located at 11:00 on a clock face centered on the nipple, is in the outer third of the breast, 3 cm from the nipple, at about the middle depth in the breast, and that it was scanned in an antiradial direction. These annotations are generated by gestures on the graphical interface, and in an additional embodiment, these labels could be selected from either a word bank, structured labels or manually entered from item 128. The labels then appear in the correct location on the image shown in the active scan 106 and also, with the exception of the scan direction, on the graphical representation 116. In a follow up scan, for each image, a dialog box may appear querying whether the lesion in the current scan is the same or a different from a lesion in a prior study. If the answer is yes, the image may be labeled with the same lesion number and location as on the prior image. The new measurements and date may then be added to the data list for that lesion. If the answer is no, a new number is assigned to the lesion along with its measurements.

The dimensions of the lesion may be measured and recorded by any means generally used. In some embodiments, a sonographer may measure the span of a lesion using their fingers. The sonographer uses their hand to pinpoint the beginning and end of a dimension of the lesion on the patient. Maintaining the position of their fingers, the sonographer places their fingers on the scale 114 on the user interface 104 and the distance between their fingers is captured. The measurement may then be dragged or otherwise manipulated to the correct spot in the graphical representation. In other embodiments, measurements may be made on the image directly. The size of a lesion may be determined by moving a cursor on the trackpad on the user interface to the desired location and tapping it to set the cursor. A second cursor is dragged to the other distance being measured, both cursors are labeled with the same number and the distance between the cursors is calculated and added to the label for the lesion. Additional measurements are labeled sequentially so that the location of a measurement between each of a pair of cursors is identifiable. In further embodiments, calipers may be placed on the screen and dragged apart using an input device such as a touch-screen to indicate the size and/or shape of a lesion. In additional embodiments, such as in obstetrics, an ellipse may be formed from two or more measurements. Such an ellipse may be further shaped using the user interface 104 to capture further measurements.

The user interface 104 may additionally include a touchpad 118 control sector which may allow for manipulation of an active scan, including allowing for zooming, changing the axial, temporal and/or lateral resolution, and moving the focal zone. In some embodiments, the displayed active ultrasound image may be copied to the touchpad. The depth of a lesion may then be captured by the processor by tapping on the lesion of interest. Such information may then be added to one or more labels on either the graphical representation of the anatomical feature and/or the active image on the display screen.

In some embodiments, the user interface 104 may include a control sector comprising image optimization controls. For example, the touchpad 118 may be bounded by a slider allowing for a change in the focal zone, depth, and frequency of the active scan. For example, in some embodiments, the upper slider on the touchpad 118 may be a cine slide 124. The slide adjacent to the touchpad 118 may be a focal zone slider 126. In further embodiments, different locations or functions may be assigned to the sliders. Properties controlled by sliders 120 may include, but are not limited to, time gain compensation, dynamic range, or frame speed. In further embodiments, additional drop down menus such as drop down menu 122 may include the most used controls for a specific type of scan. The controls listed in the drop down menus may vary depending on the type of scan selected or may be the same for all scans. In some embodiments, a drop down menu may include user preferences which may be saved under a user id and automatically populate when a user logs in. While such user preferences may refer to any desired action, in some embodiments, the user preferences may include the number of frames in a cine loop, dynamic range, field width or frame rate present for particular exam types.

In additional embodiments, the size, number, placement and content of the control sectors may be altered based on user preference. For example, while exemplary control sectors in FIG. 1 include a scale 114, a graphical representation 116, a word bank keyboard and structured labels at item 128, drop down menus 122, touchpad 118, and image optimization controls 120 and 124, more or fewer control sectors may be used. In some embodiments, an active ultrasound image or series of images may be displayed in part or over the entirety of the touch-screen user interface.

Using the user interface 104, a user may select one or more dated prior recorded ultrasound studies to be displayed as images from a first prior scan 108 or images from a second prior scan 110. Some or all of the images from the prior recorded ultrasound studies may be displayed. In some embodiments, a list is created including the selected prior recorded ultrasound studies. Any prior study may then be selected. Once selected, the area for images from a first prior scan 108 and/or images from a second prior scan 110 is populated with thumbnails of all images in the comparison scan. One or more thumbnails from the prior recorded studies may be enlarged at a time for comparison purposes. In some embodiments, the user may specify thumbnail size and the number of thumbnails displayed in preferences. If a prior study has more than one series of images, each series may be displayed in a separate row. In some embodiments, each row of images is independently scrollable or otherwise searchable.

Figure 2:
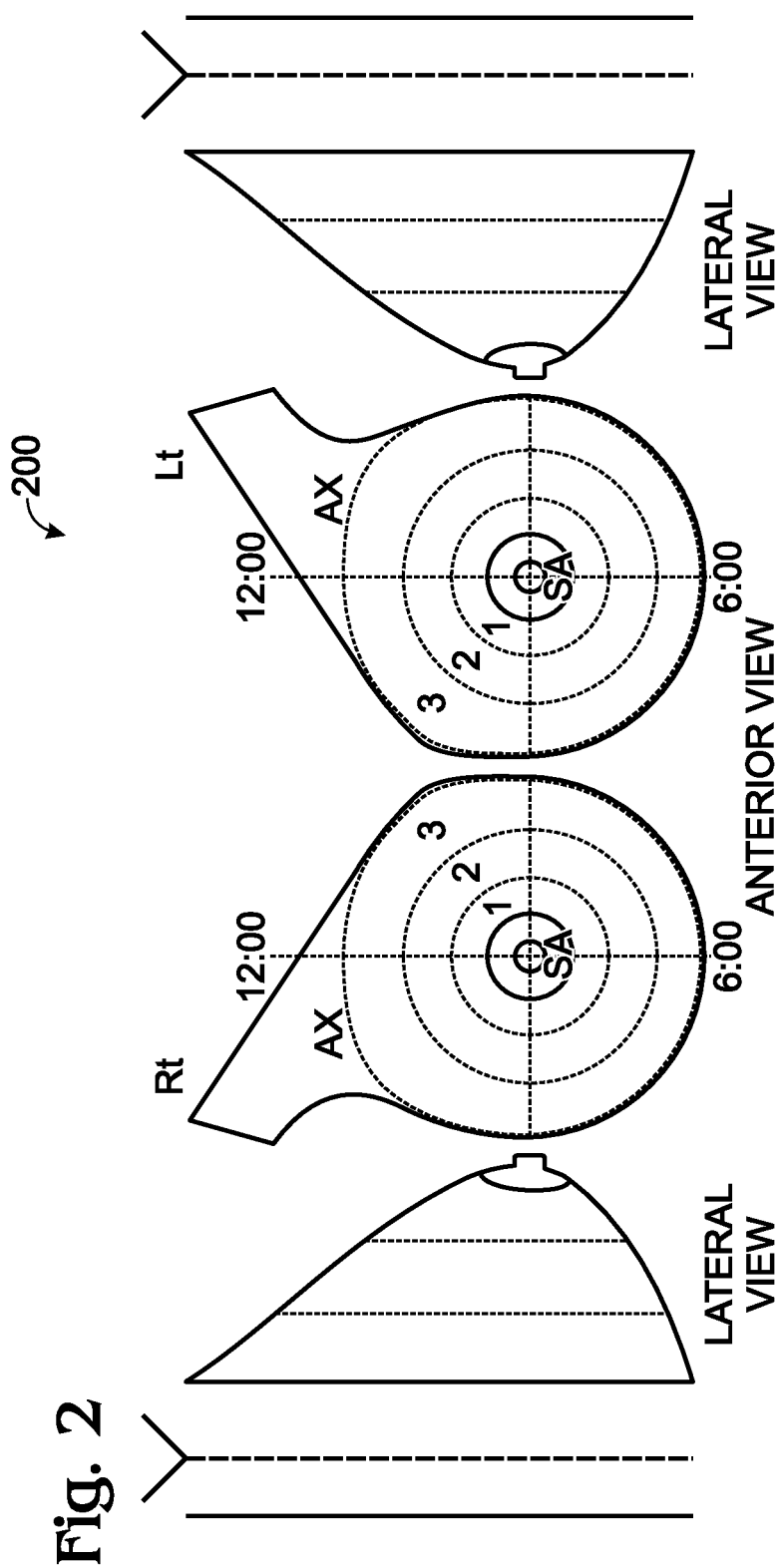
FIG. 2 is an example of a graphical representation of an anterior and lateral view of the right (RT) and left (LT) breast.

A clearer image of the graphical representation of the breast study is shown as item 200 in FIG. 2 in which the anterior and lateral views of both breasts are shown. During a scan, when either the left or right breast is chosen, in some embodiments the outline of the other breast will be removed from view to allow for more space to document findings on the breast of interest. In the anterior view of the breasts, a clock face is shown for orientation and labeling as well as distance from the nipple designated in circles 1, 2, and 3 (First ring—⅓ of breast—encompassing area just outside nipple—Zone 1, Second ring—⅔ of breast surface from nipple—Zone 2, Third ring—breast periphery—Zone 3).

Figure 3:
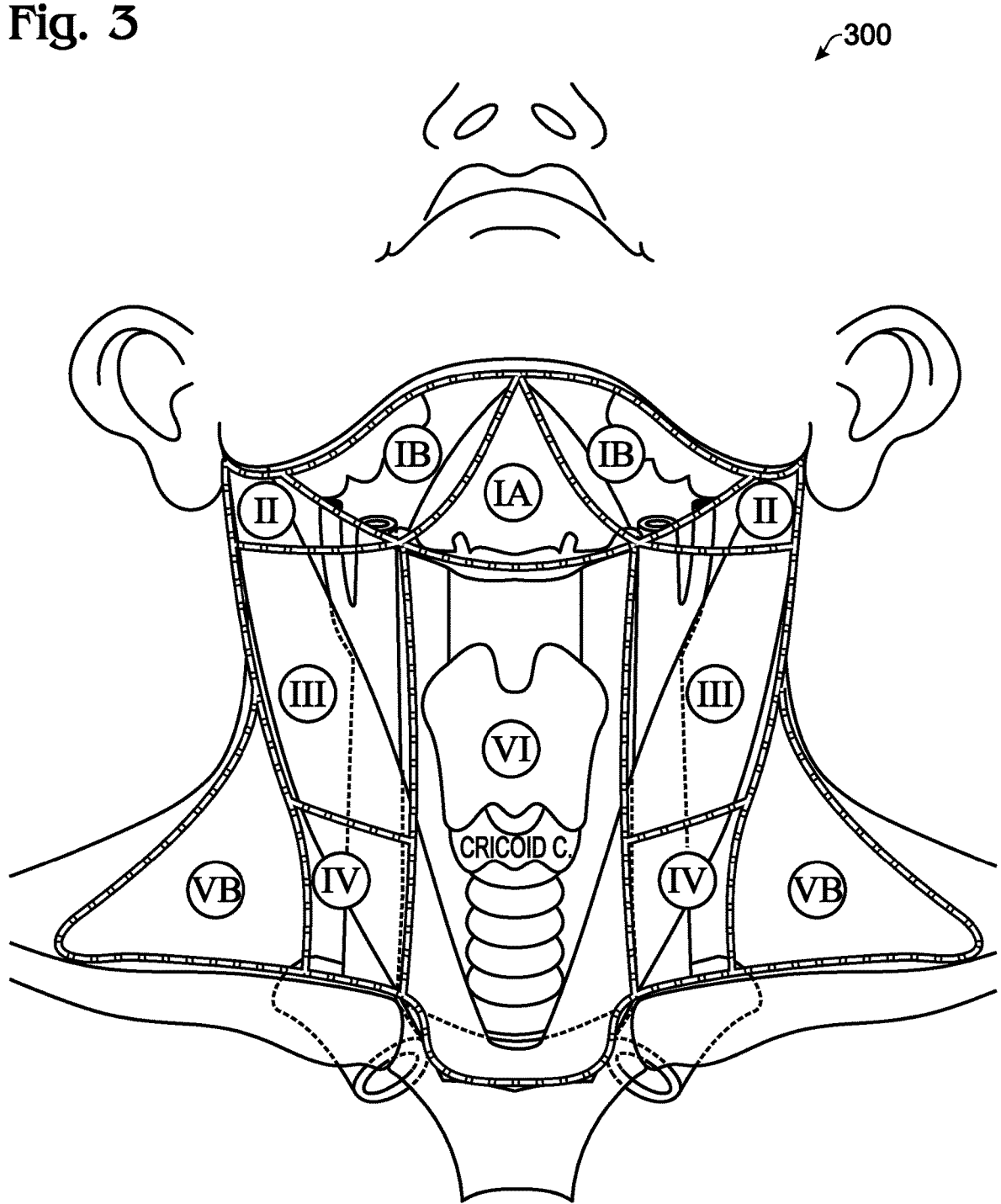
FIG. 3 illustrates an example of a graphical representation of an anterior view of anatomical zones in the neck.
Figure 4:
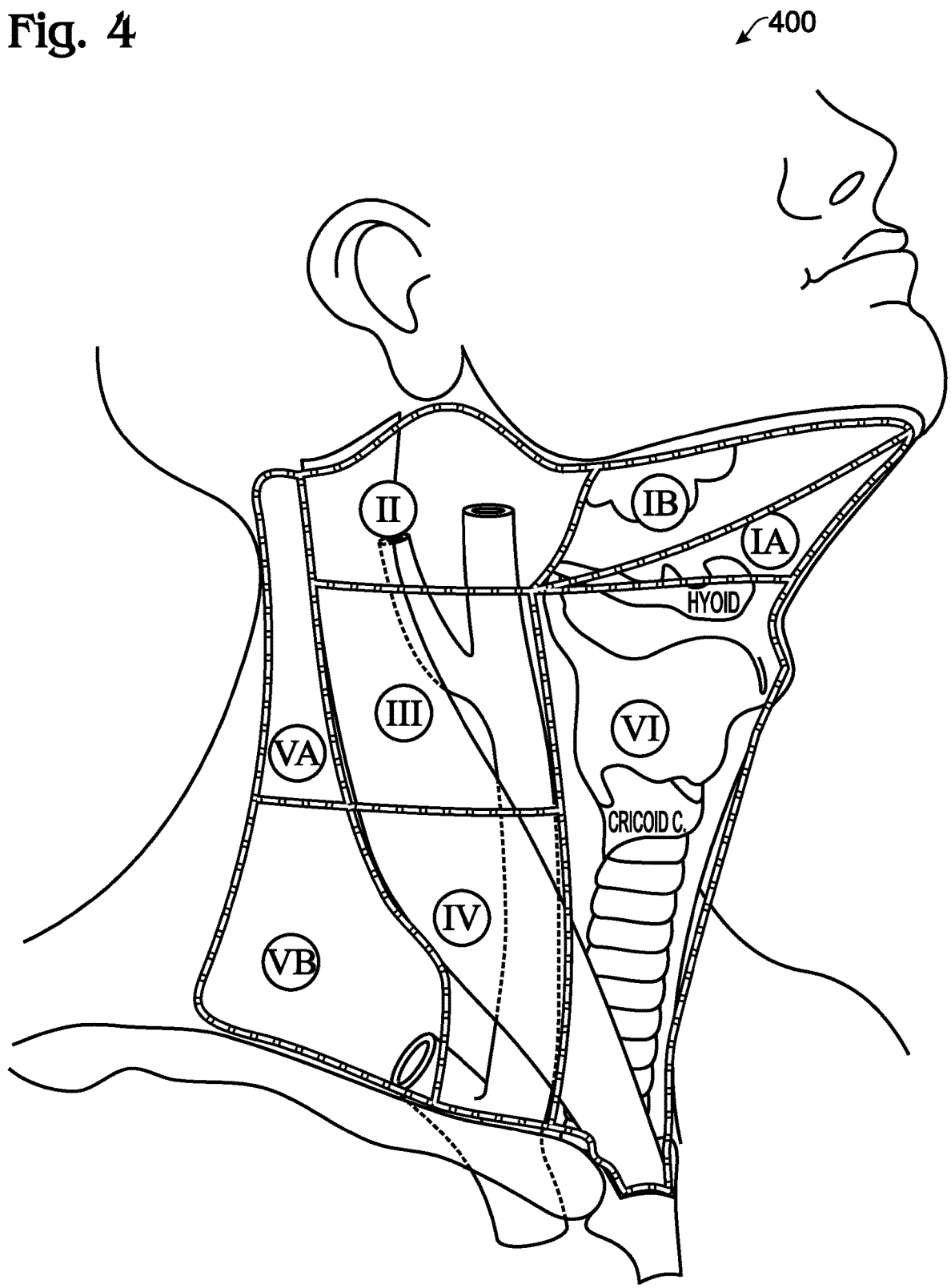
FIG. 4 illustrates an example of a graphical representation of a lateral view of anatomical zones in the neck.

As shown in FIG. 3 and FIG. 4, graphical representations of an anterior (FIG. 3) and lateral (FIG. 4) views of the neck are shown for thyroid and cervical studies. These graphical representations would appear on the user interface 104 with the labels IB, IA, II, III, IV, VA, VB and VI defining locations in the neck and appearing as options under the structured label tab where IA refers to the nodes in the submental triangle, IB refers to the submandibular triangle nodes, II refers to lymph nodes related to the upper third of the jugular vein, extending from the skull base to the inferior border of the hyoid bone with an anterior border of the stylohyoid muscle and the posterior border the sternocleidomastoid muscle, III refers to nodes located between the hyoid superiorly and a horizontal plane defined by the inferior border of the cricoid cartilage, IV refers to the posterior triangle of the neck including the spinal accessory, transverse cervical and supraclavicular group of nodes, V extends from the apex of the convergence of the sternocleidomastoid and trapezium muscle superiorly to the clavicle inferiorly, bound anteriorly by the posterior border of the sternocleidomastoid muscle and posteriorly by the anterior border of the trapezius muscle. V may be further divided by a plane defined by the inferior border of the cricoid cartilage into level VA superiorly and VB inferiorly. VI is defined by the carotid arteries laterally, the hyoid bone superiorly, and the suprasternal notch inferiorly.

Figure 5:
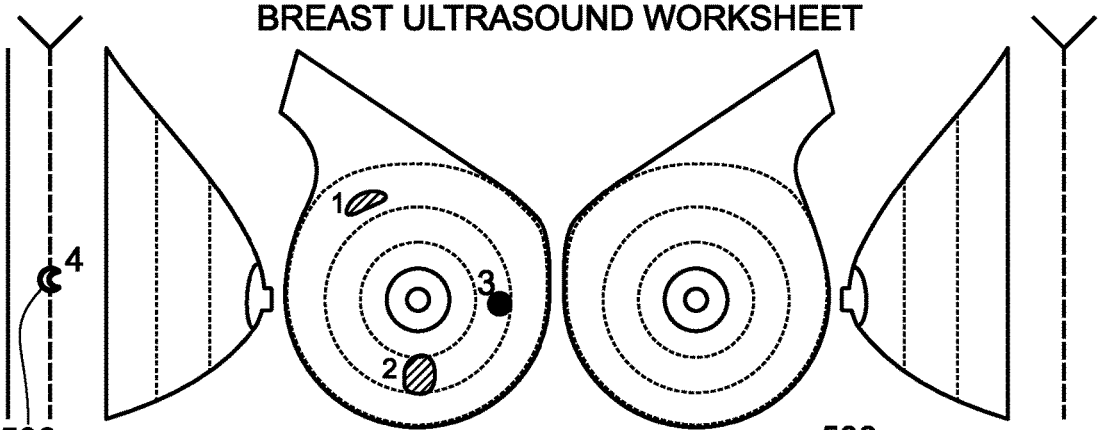
FIG. 5 illustrates an example of graphical representation of a worksheet to be read by a reader.

FIG. 5 is a representation of a worksheet which may be used for reference and/or as a final report. The worksheet shown in FIG. 5 includes identifying information for the patient at item 502, and the date of the scan at item 504. Four lesions have been identified as numbered 1, 2, 3 and 4 as shown in the graphical representation of the breast at item 506 and the lesions and types of lesions have been marked as 1. 11:00, mass, zone 3, 4 cm from nipple, posterior depth; 2. 6:00, mass, zone 2, 3 cm from nipple, middle depth; 3. 3:00, cyst, zone 2, 4 cm from nipple, anterior depth, palpable; 4. 9:00, lymph node, mid-axillary line, palpable. As this exemplary worksheet is part of a follow up exam with the reasoning for the follow up indicated at item 508, the dates and measurements of the matching lesions from the prior scans are shown at item 510 with item 4. in item 510 recording a new palp in the mid axillary line.

Figure 6:
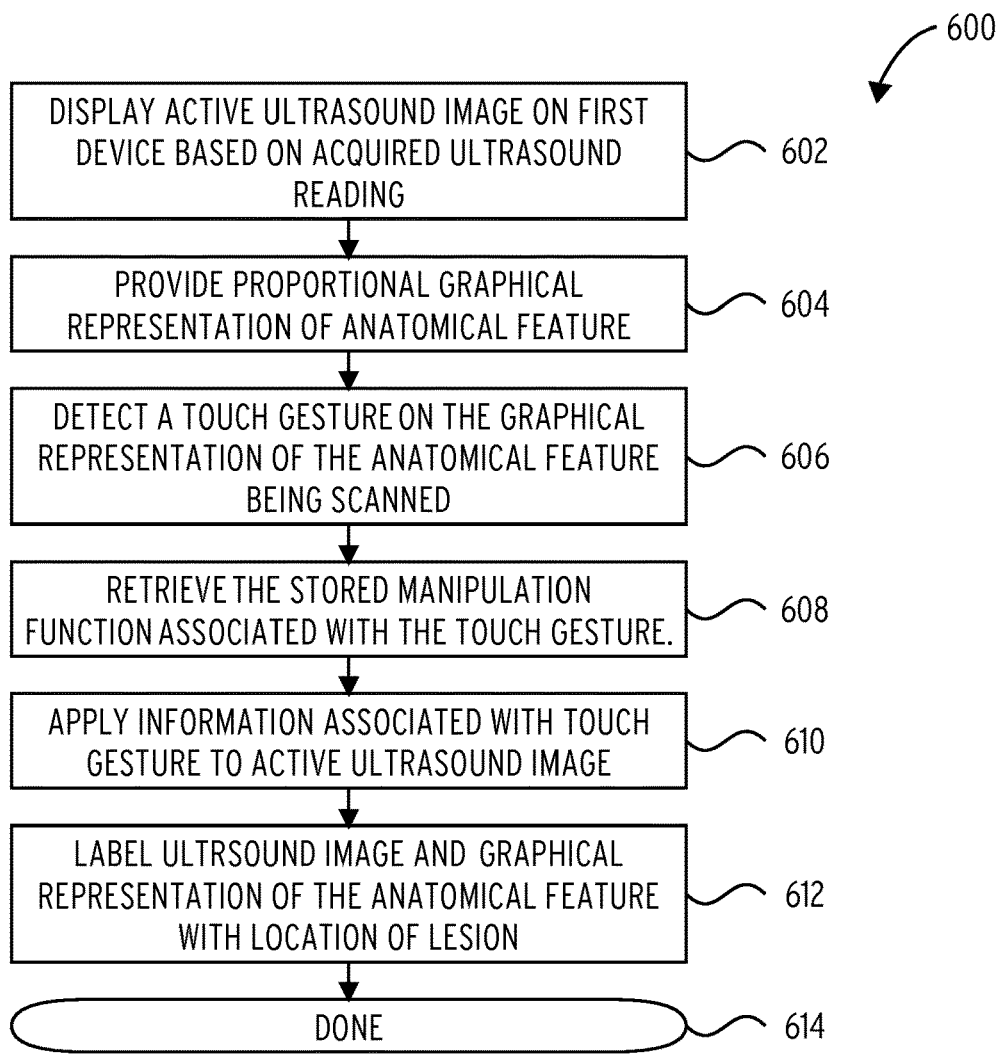
FIG. 6 illustrates a routine for inputting information onto an ultrasound image frame in an active ultrasound scan in accordance with one embodiment.
Figure 7:
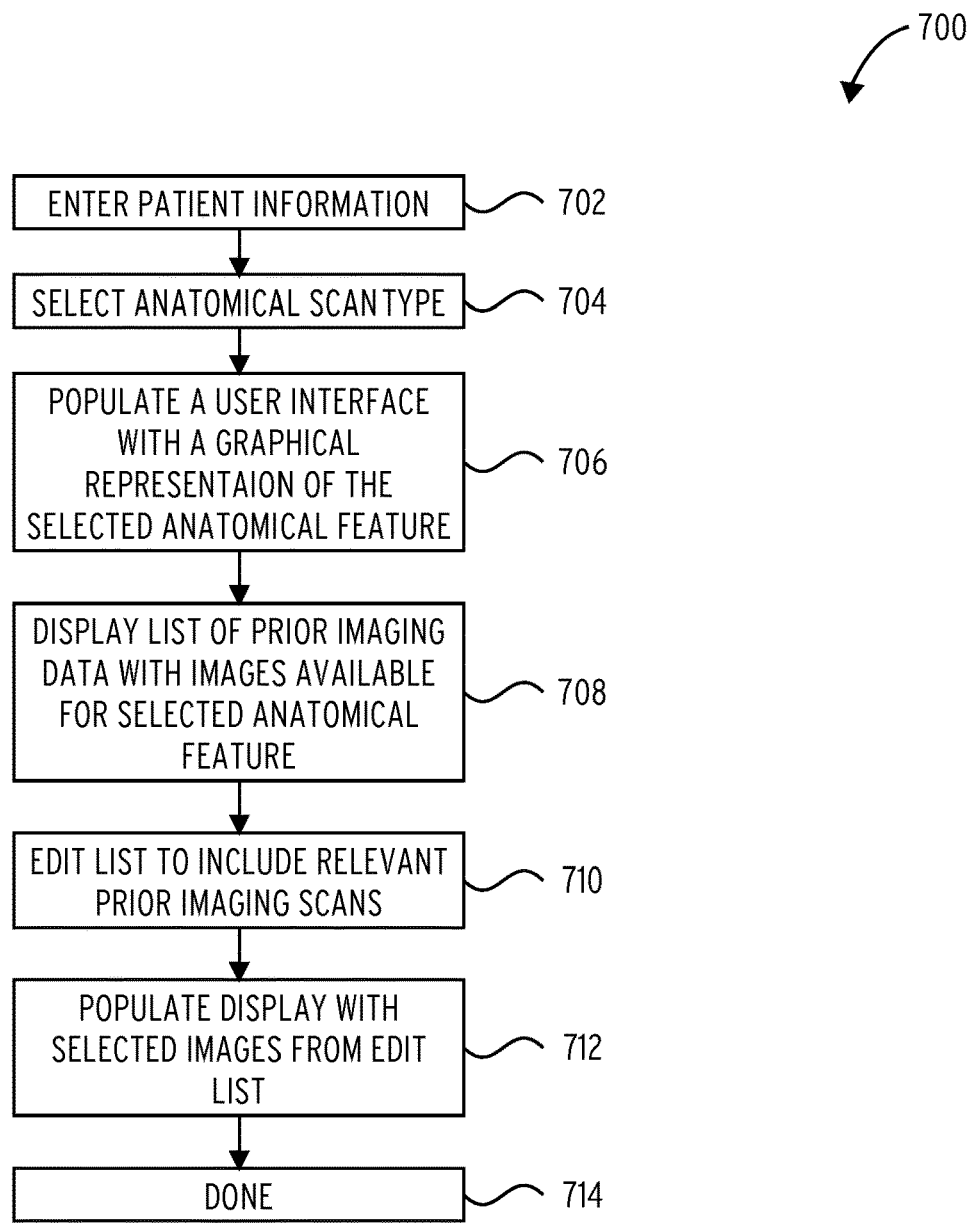
FIG. 7 illustrates a routine for selecting prior scans for comparison in accordance with one embodiment.

FIG. 6 illustrates a routine for inputting information onto an ultrasound image. In block 602, routine 600 displays an active ultrasound image on a first device based on an acquired ultrasound reading. In block 604, routine 600 provides a proportional graphical representation of the anatomical feature. In block 606, routine 600 detects a touch gesture from a user on the graphical representation of the anatomical feature being scanned. In block 608, routine 600 retrieves the stored manipulation function associated with the touch gesture. In block 610, routine 600 applies the information associated with the touch gesture to the graphical representation of the anatomical feature. In block 612, routine 600 labels the active ultrasound image and the graphical representation of the anatomical feature with the location of a lesion. In done block 614, routine 600 ends.

As shown in routine 7, patient information is entered at block 702. The anatomical scan type is selected at block 704 and a graphical representation of the anatomical feature being scanned is added to the user interface at block 706. A list of prior imaging data with images available for the anatomical feature are displayed at block 708 and the user edits the list to relevant prior imaging scans for this study at block 710. The first display is then populated with the selected images from the edited list at block 712. The routine is done at block 714.

Figure 8:
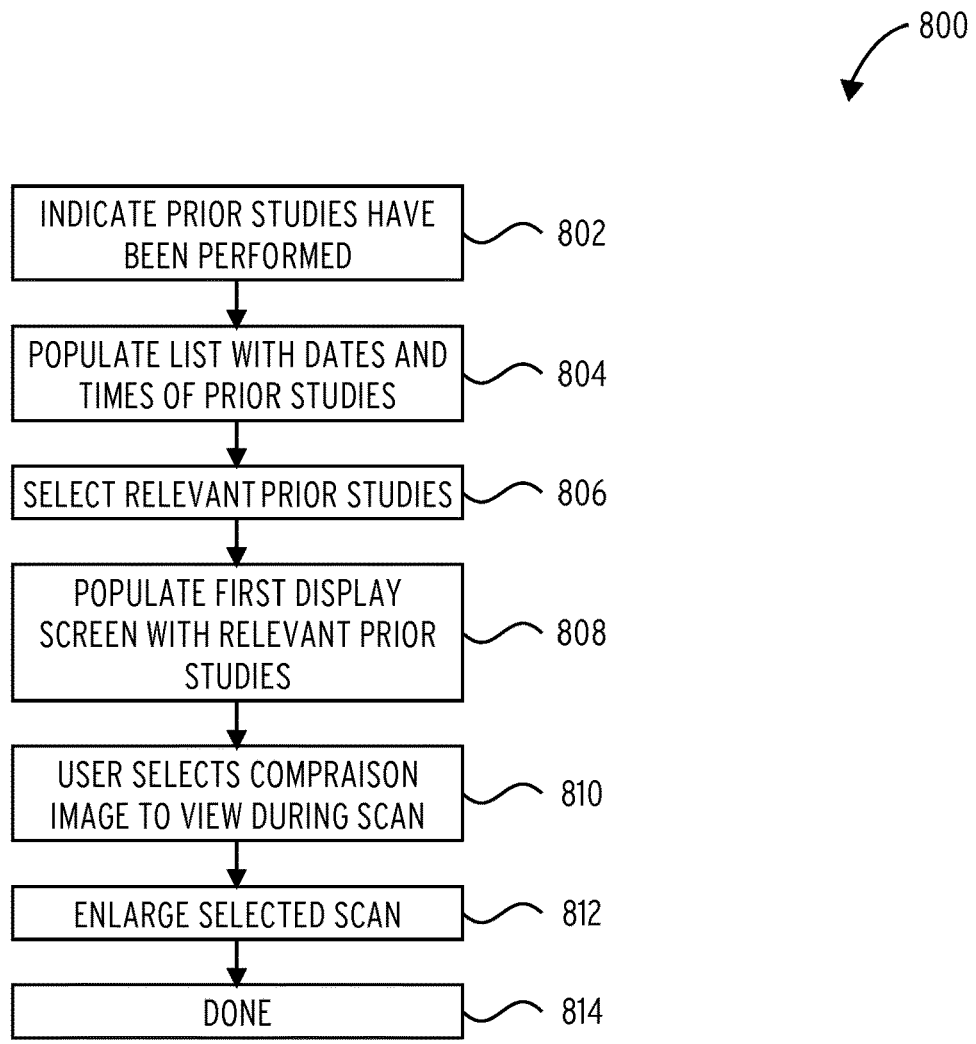
FIG. 8 illustrates a routine for the inclusion of prior results for comparison in accordance with one embodiment.
Figure 9:
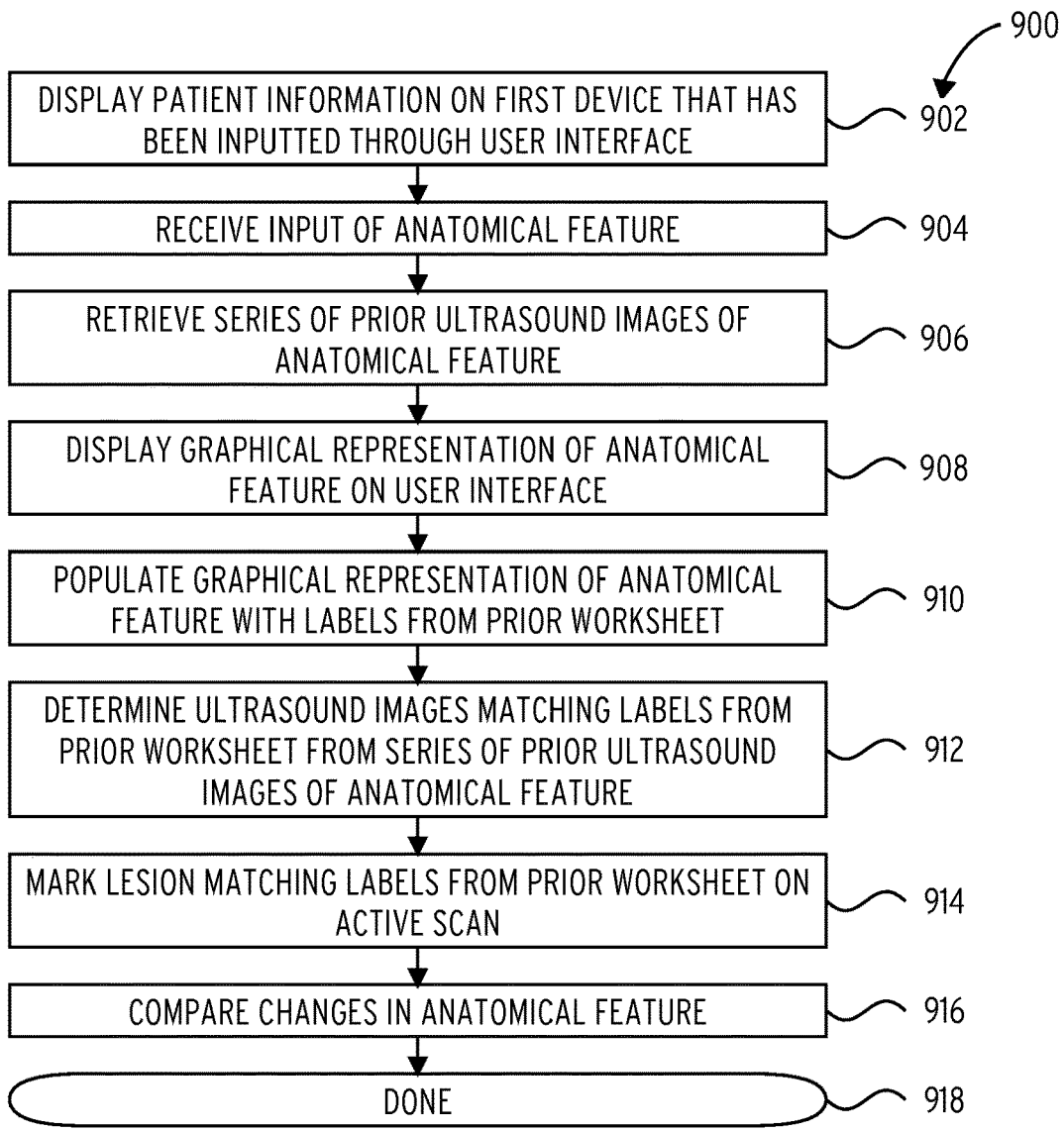
FIG. 9 illustrates a routine comparing prior studies to an active scan according to one embodiment.

FIG. 8 illustrates a routine for comparing current and prior scans. As shown in routine 800, the type of study to be performed is indicated. At block 802, a message is sent to the processor and a search is initiated for any prior scans in any medium that have been performed of this body part for this patient. A list is then populated with the dates and times of prior studies at block 804. The user then selects the relevant prior studies for the purpose of the current ultrasound scan at block 806. The first display screen is then populated with the relevant prior studies at block 808. The user selects a comparison image to view during the active scan at block 810. The selected scan is then enlarged from a thumbnail to an appropriate size for viewing and comparing to an active scan at block 812. The routine ends at done block 814.

In block 902, routine 900 displays patient information on a first device that has been inputted through a user interface. In block 904, routine 900 receives an input of the anatomical feature. In block 906, routine 900 retrieves a series of prior ultrasound images of the anatomical feature. In block 908, routine 900 displays a graphical representation of the anatomical feature on the user interface. In block 910, routine 900 populates the graphical representation of the anatomical feature with labels from a prior worksheet. In block 912, routine 900 determines the ultrasound images matching the labels from the prior worksheet from the series of prior ultrasound images of the anatomical feature. In block 914, routine 900 marks the lesion matching the labels from the prior worksheet on the active scan. In block 916, routine 900 compares changes in the anatomical feature to the prior labels. In done block 918, routine 900 ends.

Figure 10:
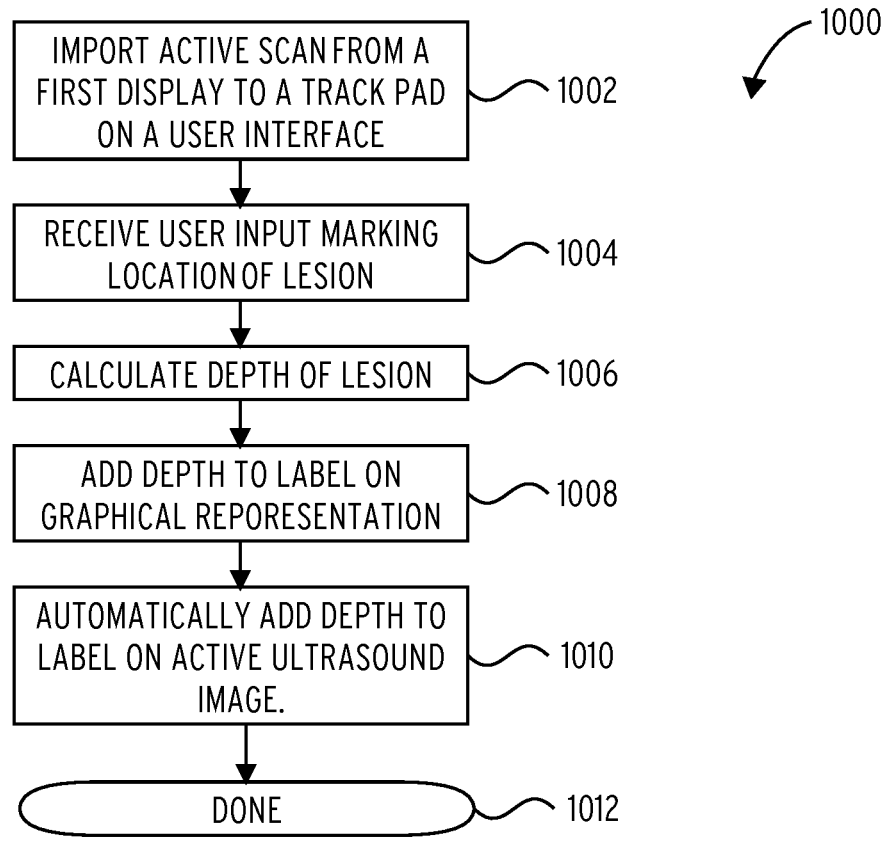
FIG. 10 illustrates a routine for determining depth of a lesion in accordance with one embodiment.

FIG. 10 illustrates a routine for determining the depth of a lesion. A captured image from an active scan is copied to a track pad on the user interface at block 1002. On the track pad, the user indicates the location of the lesion of interest at block 1004. The depth of the lesion in the frame is then captured by the system at block 1006. The depth is then added to the label on the graphical representation at block 1008 and then automatically added to the label on the displayed active ultrasound image at block 1010. The routine ends at 812.

Figure 11:
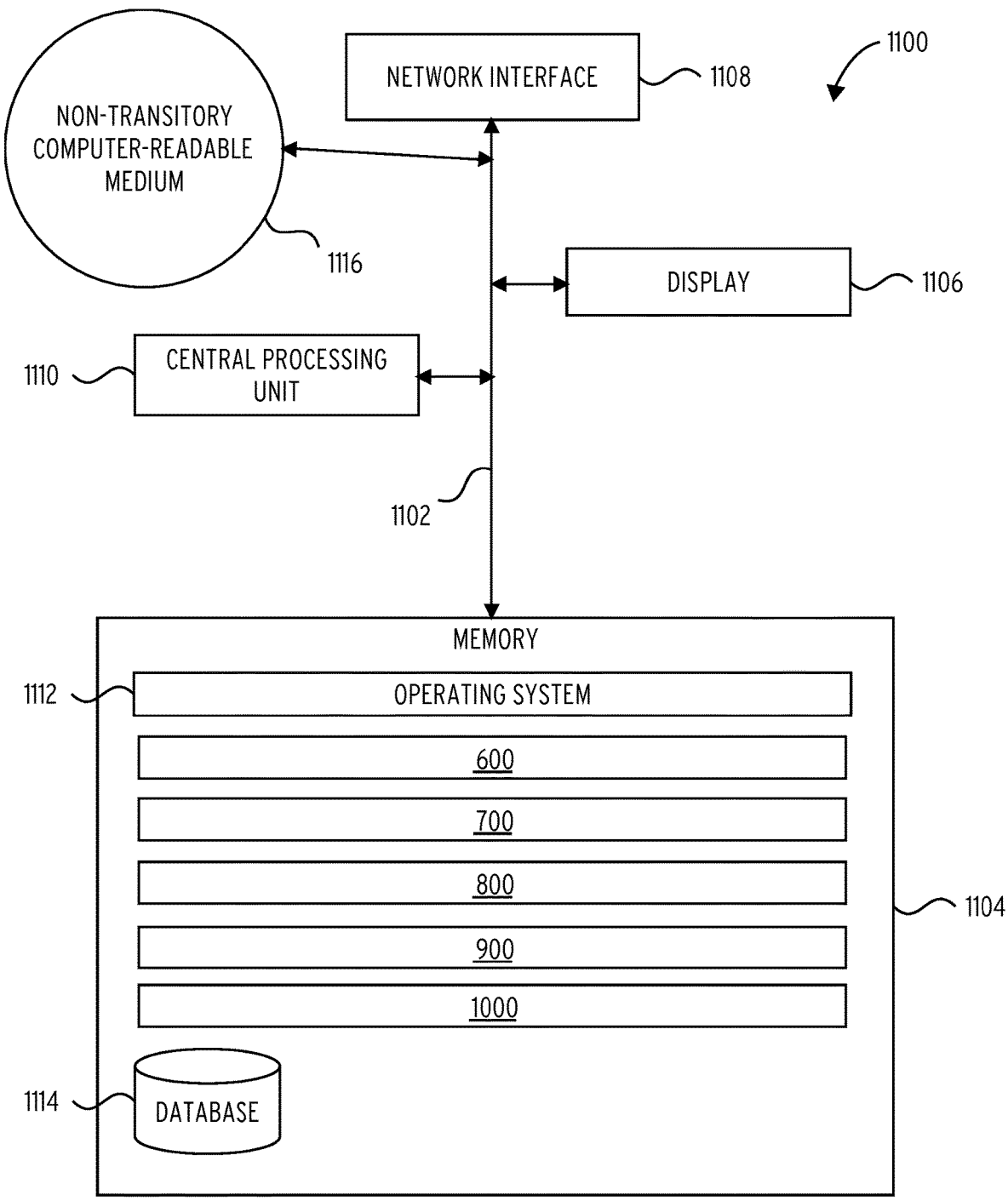
FIG. 11 illustrates a system 1100 in accordance with one embodiment.

FIG. 11 illustrates several components of an exemplary system 1100 in accordance with one embodiment. In various embodiments, system 1100 may include a desktop PC, server, workstation, mobile phone, laptop, tablet, set-top box, appliance, or other computing device that is capable of performing operations such as those described herein. In some embodiments, system 1100 may include many more components than those shown in FIG. 11. However, it is not necessary that all of these generally conventional components be shown in order to disclose an illustrative embodiment. Collectively, the various tangible components or a subset of the tangible components may be referred to herein as "logic" configured or adapted in a particular way, for example as logic configured or adapted with particular software or firmware.

In various embodiments, system 1100 may comprise one or more physical and/or logical devices that collectively provide the functionalities described herein. In some embodiments, system 1100 may comprise one or more replicated and/or distributed physical or logical devices.

In some embodiments, system 1100 may comprise one or more computing resources provisioned from a "cloud computing" provider, for example, Amazon Elastic Compute Cloud ("Amazon EC2"), provided by Amazon.com, Inc. of Seattle, Wash.; Sun Cloud Compute Utility, provided by Sun Microsystems, Inc. of Santa Clara, Calif.; Windows Azure, provided by Microsoft Corporation of Redmond, Wash., and the like.

System 1100 includes a bus 1102 interconnecting several components including a network interface 1108, a display 1106, a central processing unit 1110, and a memory 1104.

Memory 1104 generally comprises a random access memory ("RAM") and permanent non-transitory mass storage device, such as a hard disk drive or solid-state drive. Memory 1104 stores an operating system 1112.

These and other software components may be loaded into memory 1104 of system 1100 using a drive mechanism (not shown) associated with a non-transitory computer-readable medium 1116, such as a floppy disc, tape, DVD/CD-ROM drive, memory card, or the like.

Memory 1104 also includes database 1114. In some embodiments, system 1100 may communicate with database 1114 via network interface 1108, a storage area network ("SAN"), a high-speed serial bus, and/or via the other suitable communication technology.

In some embodiments, database 1114 may comprise one or more storage resources provisioned from a "cloud storage" provider, for example, Amazon Simple Storage Service ("Amazon S3"), provided by Amazon.com, Inc. of Seattle, Wash., Google Cloud Storage, provided by Google, Inc. of Mountain View, Calif., and the like.

Figure 12:
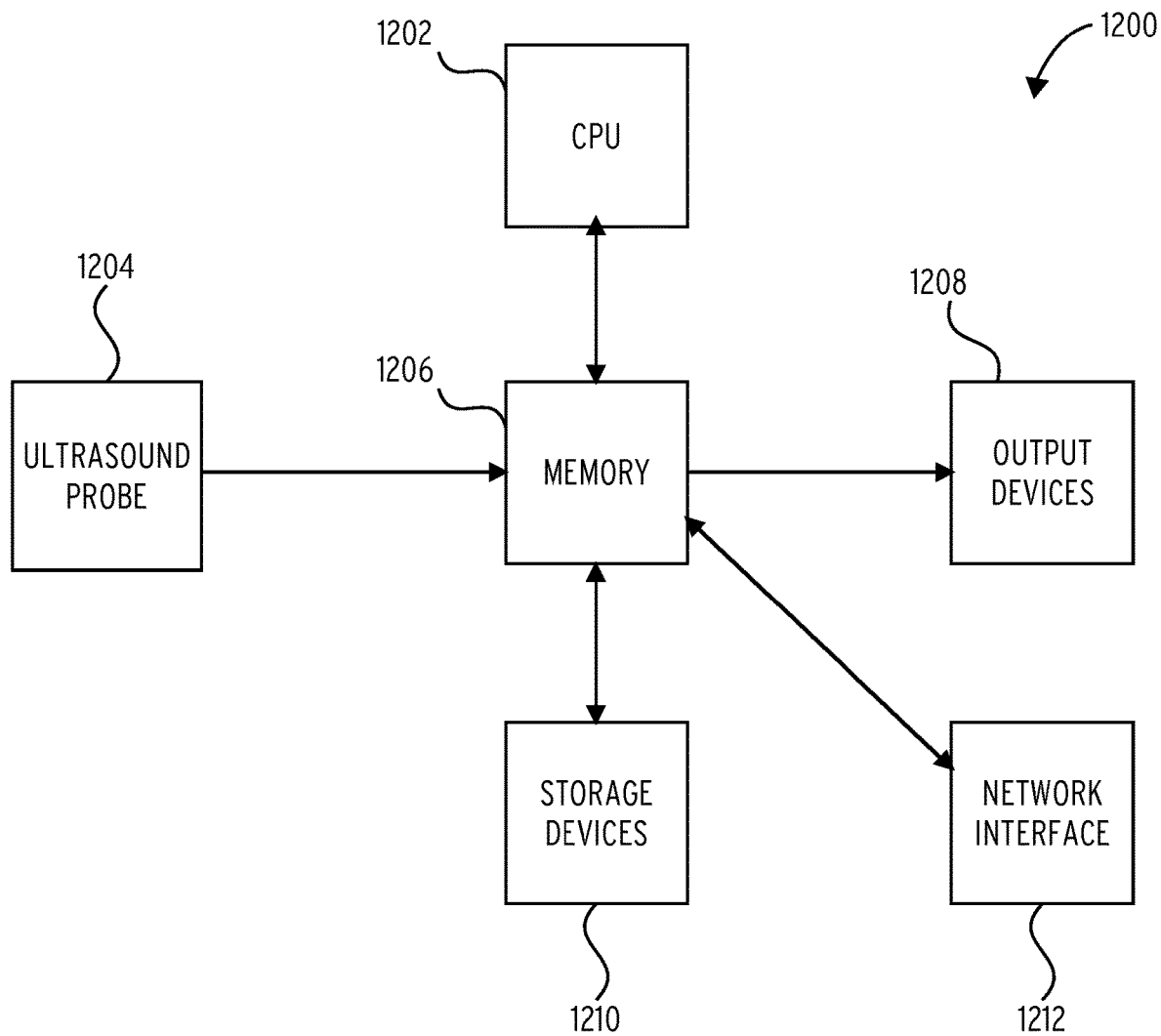
FIG. 12 illustrates an embodiment of a digital apparatus 1200 to implement components and process steps of the system described herein.

FIG. 12 illustrates an embodiment of a digital apparatus 1200 to implement components and process steps of the system described herein.

Ultrasound probe 1204 comprises transducers that convert physical phenomenon into machine internal signals, typically electrical, optical or magnetic signals. Signals may also be wireless in the form of electromagnetic radiation in the radio frequency (RF) range but also potentially in the infrared or optical range. Examples of ultrasound probe 1204 are keyboards which respond to touch or physical pressure from an anatomical feature or proximity of an anatomical feature to a surface, mice which respond to motion through space or across a plane, microphones which convert vibrations in the medium (typically air) into device signals, scanners which convert optical patterns on two or three dimensional objects into device signals. The signals from the ultrasound probe 1204 are provided via various machine signal conductors (e.g., busses or network interfaces) and circuits to memory 1206.

The memory 1206 is typically what is known as a first or second level memory device, providing for storage (via configuration of matter or states of matter) of signals received from the ultrasound probe 1204, instructions and information for controlling operation of the CPU 1202, and signals from storage devices 1210.

Information stored in the memory 1206 is typically directly accessible to the CPU 1202 of the device. Signals input to the device cause the reconfiguration of the internal material/energy state of the memory 1206, creating in essence a new machine configuration, influencing the behavior of the digital apparatus 1200 by affecting the behavior of the CPU 1202 with control signals (instructions) and data provided in conjunction with the control signals.

Second or third level storage devices 1210 may provide a slower but higher capacity machine memory capability. Examples of storage devices 1210 are hard disks, optical disks, large capacity flash memories or other non-volatile memory technologies, and magnetic memories.

The CPU 1202 may cause the configuration of the memory 1206 to be altered by signals in storage devices 1210. In other words, the CPU 1202 may cause data and instructions to be read from storage devices 1210 in the memory 1206 from which may then influence the operations of CPU 1202 as instructions and data signals, and from which it may also be provided to the output devices 1208. The CPU 1202 may alter the content of the memory 1206 by signaling to a machine interface of memory 1206 to alter the internal configuration, and then converted signals to the storage devices 1210 to alter its material internal configuration. In other words, data and instructions may be backed up from memory 1206, which is often volatile, to storage devices 1210, which are often non-volatile.

Output devices 1208 are transducers which convert signals received from the memory 1206 into physical phenomenon such as vibrations in the air, or patterns of light on a machine display, or vibrations (i.e., haptic devices) or patterns of ink or other materials (i.e., printers and 3-D printers).

The network interface 1212 receives signals from the memory 1206 and converts them into electrical, optical, or wireless signals to other machines, typically via a machine network. The network interface 1212 also receives signals from the machine network and converts them into electrical, optical, or wireless signals to the memory 1206.

References to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to a single one or multiple one. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list, unless expressly limited to one or the other.

"Logic" refers to machine memory circuits, non-transitory machine readable media, and/or circuitry which by way of its material and/or material-energy configuration comprises control and/or procedural signals, and/or settings and values (such as resistance, impedance, capacitance, inductance, current/voltage ratings, etc.), that may be applied to influence the operation of a device. Magnetic media, electronic circuits, electrical and optical memory (both volatile and nonvolatile), and firmware are examples of logic. Logic specifically excludes pure signals or software per se (however does not exclude machine memories comprising software and thereby forming configurations of matter). Those skilled in the art will appreciate that logic may be distributed throughout one or more devices, and/or may be comprised of combinations of memory, media, processing circuits and controllers, other circuits, and so on. Therefore, in the interest of clarity and correctness logic may not always be distinctly illustrated in drawings of devices and systems, although it is inherently present therein.

The techniques and procedures described herein may be implemented via logic distributed in one or more computing devices. The particular distribution and choice of logic will vary according to implementation. Those having skill in the art will appreciate that there are various logic implementations by which processes and/or systems described herein can be effected (e.g., hardware, software, and/or firmware), and that the preferred vehicle will vary with the context in which the processes are deployed. "Software" refers to logic that may be readily readapted to different purposes (e.g. read/write volatile or nonvolatile memory or media). "Firmware" refers to logic embodied as read-only memories and/or media. Hardware refers to logic embodied as analog and/or digital circuits. If an implementer determines that speed and accuracy are paramount, the implementer may opt for a hardware and/or firmware vehicle; alternatively, if flexibility is paramount, the implementer may opt for a solely software implementation; or, yet again alternatively, the implementer may opt for some combination of hardware, software, and/or firmware. Hence, there are several possible vehicles by which the processes described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations may involve optically-oriented hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood as notorious by those within the art that each function and/or operation within such block diagrams, flowcharts, or examples can be implemented, individually and/or collectively, by a wide range of hardware, software, firmware, or virtually any combination thereof. Several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, flash drives, SD cards, solid state fixed or removable storage, and computer memory. In a general sense, those skilled in the art will recognize that the various aspects described herein which can be implemented, individually and/or collectively, by a wide range of hardware, software, firmware, or any combination thereof can be viewed as being composed of various types of "circuitry." Consequently, as used herein "circuitry" includes, but is not limited to, electrical circuitry having at least one discrete electrical circuit, electrical circuitry having at least one integrated circuit, electrical circuitry having at least one application specific integrated circuit, circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), circuitry forming a memory device (e.g., forms of random access memory), and/or circuitry forming a communications device (e.g., a modem, communications switch, or optical-electrical equipment).

Those skilled in the art will recognize that it is common within the art to describe devices and/or processes in the fashion set forth herein, and thereafter use standard engineering practices to integrate such described devices and/or processes into larger systems. That is, at least a portion of the devices and/or processes described herein can be integrated into a network processing system via a reasonable amount of experimentation.

The foregoing described aspects depict different components contained within, or connected with different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

Embodiments of methods and systems for an ultrasound system have been described. The following claims are directed to said embodiments, but do not preempt ultrasound systems in the abstract. Those having skill in the art will recognize numerous other approaches to ultrasound systems, precluding any possibility of preemption in the abstract. However, the claimed system improves, in one or more specific ways, the operation of an ultrasound system, and thus distinguishes from other approaches to the same problem/process in how its physical arrangement of a machine system determines the system's operation and ultimate effects on the material environment. The terms used in the appended claims are defined herein in the glossary section, with the proviso that the claim terms may be used in a different manner if so defined by express recitation.

What is claimed is:

1. A method for annotating an ultrasound image frame in an active ultrasound scan of an anatomical feature comprising:
    displaying on a display screen of a first device a first active ultrasound image that includes an anatomical feature;
    displaying a proportional graphical representation of the anatomical feature on a user interface comprising a touch-screen, the displayed graphical representation being displayed separately from the first active ultrasound image displayed on the first device display screen;
    detecting, from a user, a touch gesture on the user interface;
    correlating the touch gesture on the user interface with a stored image manipulation function, wherein each of a plurality of touch gestures is correlated to a different image manipulation function;
    applying the image manipulation function associated with the touch gesture to the active ultrasound image and to the graphical representation of the anatomical feature being scanned, wherein information associated with the touch gesture on the user interface manipulates the active ultrasound image;

labeling the graphical representation of the anatomical feature with a location of a lesion or other imaged feature of interest, wherein a label applied to the graphical representation of the anatomical feature on the user interface appears on the active ultrasound image that is being displayed on the display screen; and wherein subsequent touch gestures on the user interface modify the label of the lesion on the displayed active ultrasound image.

2. The method of claim 1, further comprising importing the active ultrasound image to a touchpad on the user interface, wherein by tapping on the lesion on the touchpad, a relative depth of the lesion in an image frame of the anatomical feature is captured.

3. The method of claim 1, wherein image optimization controls on the user interface are used to alter image properties on the first device.

4. The method of claim 3, wherein the image optimization controls are a focal zone, a time gain compensation, a dynamic range, a frame rate, a Doppler gain, and a field width of the active ultrasound scan.

5. The method of claim 1, wherein the first device further displays manipulable thumbnails of prior scans of the anatomical feature under examination.

6. The method of claim 1, wherein the first device further displays thumbnails of captured image frames from the active ultrasound image.

7. The method of claim 1, wherein an additional annotation is applied to the label applied to the ultrasound image, wherein the additional annotation is one or more of a depth of the lesion or other imaged feature of interest, a number of lesions or other imaged feature of interest, a type of lesion or type of other imaged feature of interest, or a distance of the lesion or other imaged feature of interest from anatomical landmarks.

8. The method of claim 1, wherein the user interface is used to adjust a time gain compensation of the active ultrasound image.

9. The method of claim 1, wherein the label applied to the ultrasound image is chosen from a word bank, set of structured labels, or manual entry.

10. The method of claim 1, further comprising generating a worksheet including information regarding the anatomical feature captured on the active ultrasound image on the first display screen and the graphical representation of the anatomical feature on the user interface.

11. The method of claim 1, wherein a size of the lesion may be captured through a two finger gesture on a scale on the user interface.

12. A method of comparing prior images of an anatomical feature with an active scan, the method comprising:

displaying patient information on a first device that has been inputted through a user interface, wherein the user interface is a touch-screen;

receiving an input of an active scan ultrasound image that includes the anatomical feature being scanned;

displaying the active scan ultrasound image that includes the anatomical feature being scanned on a display screen;

retrieving a series of prior generated ultrasound images of the anatomical feature, wherein the prior generated ultrasound images are displayed adjacent to the active scan;

displaying a graphical representation of the anatomical feature on the user interface, the graphical representation displayed separately from the active scan;

populating the graphical representation of the anatomical feature with labels from a prior generated worksheet;

determining ultrasound images, from the series of prior generated ultrasound images of the anatomical feature, having labels that match labels from the prior generated worksheet;

marking a lesion, or other feature of interest, matching the labels from the prior generated worksheet on the active scan; and comparing changes in the anatomical feature being scanned with the labels from a single previous ultrasound image, wherein the labels on the graphical representation are amended to indicate the current labels on the active scan.

13. The method of claim 12, wherein the changes are at least one of additional lesions or other imaged features of interest, change in size, or change in composition.

14. The method of claim 12, further comprising:

in response to a user input placing a label on the graphical representation of the anatomical feature, retrieving previous ultrasound images having labels equivalent to the label placed on the graphical representation of the anatomical feature.

15. The method of claim 12, further comprising receiving an input at the user interface to adjust an image property of the active scan.

16. An ultrasound system, comprising:

an ultrasound probe comprising a transducer configured to transmit an ultrasound signal to a target object, receive an ultrasound echo signal reflected from the target object, and form ultrasound data corresponding to the target object;

a first processor configured to form an ultrasound image from the ultrasound data;

a first display screen;

a touch-screen user interface;

a second processor that receives input from the touch-screen user interface; and wherein in response to receiving input from the touch-screen user interface, the second processor sends a signal to a labeling module to input labels and measurements of the target object on both of the ultrasound image displayed on the first display screen and on a graphical representation of the target object displayed on a user interface.

17. The ultrasound system of claim 16, wherein the touch-screen user interface comprises at least one control sector.

18. The ultrasound system of claim 17, wherein the at least one control sectors are the graphical representation of the anatomical feature being scanned, a track pad, a word bank, a structured label bank, a keyboard, a touch-screen, a scale, an active ultrasound image or image optimization controls.

19. The ultrasound system of claim 16, wherein the touch-screen user interface further comprises a series of drop-down menus with additional control options.

20. An ultrasound system, comprising:

an ultrasound probe comprising a transducer configured to transmit an ultrasound signal to a target object, receive an ultrasound echo signal reflected from the target object, and form ultrasound data corresponding to the target object;

a first processor configured to form an ultrasound image from the ultrasound data;

a first display screen, the first display screen divided into a plurality of sectors, each sector displaying different information, wherein the information is an active scan, captured images from the active scan, and images from previous scans of a same anatomical feature of a same individual;

a touch-screen user interface;

a second processor that receives input from the touch-screen user interface; and wherein in response to receiving input from the touch-screen user interface, the second processor sends a signal to a labeling module to input labels and measurements of the target object on an image on the first display screen and a graphical representation of an anatomical being scanned on a user interface.

21. An ultrasound system, comprising:

an ultrasound probe comprising a transducer configured to transmit an ultrasound signal to a target object, receive an ultrasound echo signal reflected from the target object, and form ultrasound data corresponding to the target object;

a first processor configured to form an ultrasound image from the ultrasound data;

a first display screen, a touch-screen user interface, wherein the touch-screen user interface further comprises a measuring apparatus that calculates a distance between two fingers placed on the measuring apparatus and places a measurement for an anatomical feature being scanned on the ultrasound image and on a label on the graphical representation of the anatomical feature being scanned;

a second processor that receives input from the touch-screen user interface; and wherein in response to receiving input from the touch-screen user interface, the second processor sends a signal to a labeling module to input labels and measurements of the target object on an image on the first display screen and a graphical representation of an anatomical being scanned on a user interface.

* * * * *

UNITED STATES PATENT AND TRADEMARK OFFICE
CERTIFICATE OF CORRECTION

PATENT NO. : 10,499,882 B2
APPLICATION NO. : 15/200609
DATED : December 10, 2019
INVENTOR(S) : Valerie Hunter et al.

Page 1 of 1

It is certified that error appears in the above-identified patent and that said Letters Patent is hereby corrected as shown below:

On the Title Page

Item (56), under References Cited, delete "12,097,626" and insert --2008/0306385 A1--.

In the Specification

In Column 3, Line 61, delete "columns.'" and insert --columns'.--.

Signed and Sealed this
Twenty-sixth Day of May, 2020

Andrei Iancu
*Director of the United States Patent and Trademark Office*